(12) United States Patent
Liu

(10) Patent No.: US 11,298,474 B2
(45) Date of Patent: Apr. 12, 2022

(54) ELECTRONIC CIGARETTE

(71) Applicant: Tuanfang Liu, Shenzhen (CN)

(72) Inventor: Tuanfang Liu, Shenzhen (CN)

( * ) Notice: Subject to any disclaimer, the term of this patent is extended or adjusted under 35 U.S.C. 154(b) by 422 days.

(21) Appl. No.: 16/572,571

(22) Filed: Sep. 16, 2019

(65) Prior Publication Data

US 2020/0315262 A1     Oct. 8, 2020

(30) Foreign Application Priority Data

Apr. 2, 2019    (CN) .......................... 201910262669.0
Apr. 2, 2019    (CN) .......................... 201920444574.6

(51) Int. Cl.
*A24F 13/00*     (2006.01)
*A24F 17/00*     (2006.01)
*A24F 25/00*     (2006.01)
*A61M 11/04*     (2006.01)
*A24B 15/167*    (2020.01)

(52) U.S. Cl.
CPC .......... *A61M 11/042* (2014.02); *A24B 15/167* (2016.11); *A61M 2205/8206* (2013.01)

(58) Field of Classification Search
CPC .......... A24F 40/10; A24F 40/40; A24F 40/49; A61M 11/042; A61M 2205/8206; A24B 15/167
See application file for complete search history.

(56) References Cited

U.S. PATENT DOCUMENTS

| 2017/0311384 | A1* | 10/2017 | Wu ...................... A61M 11/042 |
| 2017/0354182 | A1* | 12/2017 | Liu ......................... A24F 40/40 |
| 2018/0085551 | A1* | 3/2018 | Krietzman ........... H05B 1/0252 |
| 2018/0263294 | A1* | 9/2018 | Qiu ......................... A24F 40/85 |
| 2019/0037922 | A1* | 2/2019 | Liu ........................... H05B 3/44 |

* cited by examiner

*Primary Examiner* — Abdullah A Riyami
*Assistant Examiner* — Thang H Nguyen
(74) *Attorney, Agent, or Firm* — Matthias Scholl P.C.; Matthias Scholl

(57) ABSTRACT

An electronic cigarette including an atomization assembly and a battery assembly. The atomization assembly includes a mouthpiece; a first spring disposed in a cavity of the mouthpiece; a first connection ring; a first seal ring sealing the first connection ring; a first fixed seat fixing the mouthpiece; a silicone gasket; a hollow rod; a first fixed ring fixing the hollow rod; a glass tube; a second seal ring and a third seal ring sealing two ends of the glass tube, respectively; a second fixed ring fixing the glass tube; an atomizer; a regulating ring; a second fixed seat fixing the atomizer; a fourth seal ring and a fifth seal ring sealing two ends of the second fixed seat, respectively; a second spring; a first threaded ring; a first insulation ring being sheathed on the atomizer; and a first joint directly connected to the atomizer.

1 Claim, 5 Drawing Sheets

ELECTRONIC CIGARETTE

CROSS-REFERENCE TO RELATED APPLICATIONS

Pursuant to 35 U.S.C. § 119 and the Paris Convention Treaty, this application claims foreign priority to Chinese Patent Application No. 201910262669.0 filed Apr. 2, 2019, and to Chinese Patent Application No. 201920444574.6 filed Apr. 2, 2019. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND

The disclosure relates to an electronic cigarette.

Electronic cigarettes atomize e-liquid.

Conventionally, the atomization assembly of electronic cigarettes includes no structures to prevent accidental disassembly. This results in unwanted leakage of the e-liquid.

In addition, conventionally, the atomization assembly is fixedly attached to the battery assembly resulting in difficult replacement or repair of individual parts.

SUMMARY

The disclosure provides an electronic cigarette.

The electronic cigarette comprises an atomization assembly and a battery assembly.

The atomization assembly comprises a mouthpiece; a first spring disposed in a cavity of the mouthpiece; a first connection ring; a first seal ring sealing the first connection ring; a first fixed seat fixing the mouthpiece; a silicone gasket; a hollow rod; a first fixed ring fixing the hollow rod; a glass tube; a second seal ring and a third seal ring sealing two ends of the glass tube, respectively; a second fixed ring fixing the glass tube; an atomizer; a regulating ring; a second fixed seat fixing the atomizer; a fourth seal ring and a fifth seal ring sealing two ends of the second fixed seat, respectively; a second spring; a first threaded ring; a first insulation ring being sheathed on the atomizer; and a first joint directly connected to the atomizer.

The battery assembly comprises a cover plate; a plurality of first screws fixing the cover plate; a power button; a button board; a support; a housing; a second threaded ring; a second connection ring; a press plate; a press key; a silicone cap; a base cover; a plurality of second screws fixing the base cover; a second joint; a second spring; a second insulation ring; a third fixed ring fixing the second joint; a magnet; a fifth fixed ring fixing the magnet; a sixth seal ring; an elastic fixed seat fixing the second joint; an e-liquid blocker; a battery core; and a third connection ring connected to a negative end of the battery core.

The first seal ring is disposed on one end of the first connection ring; the one end of the first connection ring is directly connected to the first fixed seat fixing the mouthpiece; the first spring is sheathed on the first connection ring; the mouthpiece is fixed on the first fixed seat; the silicone gasket and the second seal ring are disposed on the first fixed ring; the first fixed seat is in threaded connection to the first fixed ring; the first fixed ring is in threaded connection to the glass tube; the hollow rod is disposed on the second fixed ring; the third seal ring is sheathed on the second fixed ring; the second fixed ring is disposed in the glass tube; the first insulation ring is sheathed on the first joint; the first joint is disposed in the first threaded ring.

The second spring is disposed on the first threaded ring; the first threaded ring is disposed in the second fixed seat; the fourth seal ring and the fifth seal ring are disposed on two ends of the second fixed seat, respectively; the regulating ring is sheathed on the second fixed seat; the atomizer is in threaded connection to the second fixed seat; and the second fixed seat is in threaded connection to the second fixed ring; the second spring is sheathed on the third fixed ring; the second joint is fixed on the third fixed ring; the second insulation ring is sheathed on the second joint and disposed in the fifth fixed ring; the fifth fixed ring is disposed in the magnet; the magnet is disposed in the elastic fixed seat; the e-liquid blocker is disposed on one end of the third fixed ring; the third connection ring is directly connected to the elastic fixed seat; the sixth seal ring is disposed on the elastic fixed seat; the elastic fixed seat is disposed in the housing; the battery core is disposed in the housing; the second connection ring is disposed in the second threaded ring and is in magnetic connection to the magnet; the power button is disposed on the button board; the button board is disposed on the support; the support is disposed in the housing; the cover plate is fixed on the housing via the plurality of first screws; and the silicone cap is disposed on the press key; the press key is disposed on the press plate; the press plate is disposed on the base cover; and the base cover is fixed on the housing via the plurality of second screws.

In the upper part of the atomization assembly, the first fixed seat is in threaded connection to the first fixed ring, which forms a first locking structure. In the lower part of the atomization assembly, the atomizer is in threaded connection to the second fixed seat, and the second fixed seat is in threaded connection to the second fixed ring, which forms a second locking structure. Thus, the atomization assembly is an integrated structure and is not easy to dismantle by children. This reduces the risk of e-liquid leakage.

The atomization assembly is disposed in the housing of the battery assembly. Specifically, the atomization assembly is in threaded connection to the second threaded ring, and the second threaded ring is in magnetic connection to the magnet, so that the atomization assembly is connected to the battery assembly through magnetic attraction. This simplifies the separation of the atomization assembly from the battery assembly.

Advantages of the electronic cigarette according to embodiments of the disclosure are summarized as follows. The atomization assembly is an integrated structure and is not easy to dismantle by children. This reduces the risk of e-liquid leakage. The atomization assembly is connected to the battery assembly through magnetic attraction. This simplifies the separation of the atomization assembly from the battery assembly.

DETAILED DESCRIPTION

Figure 1:
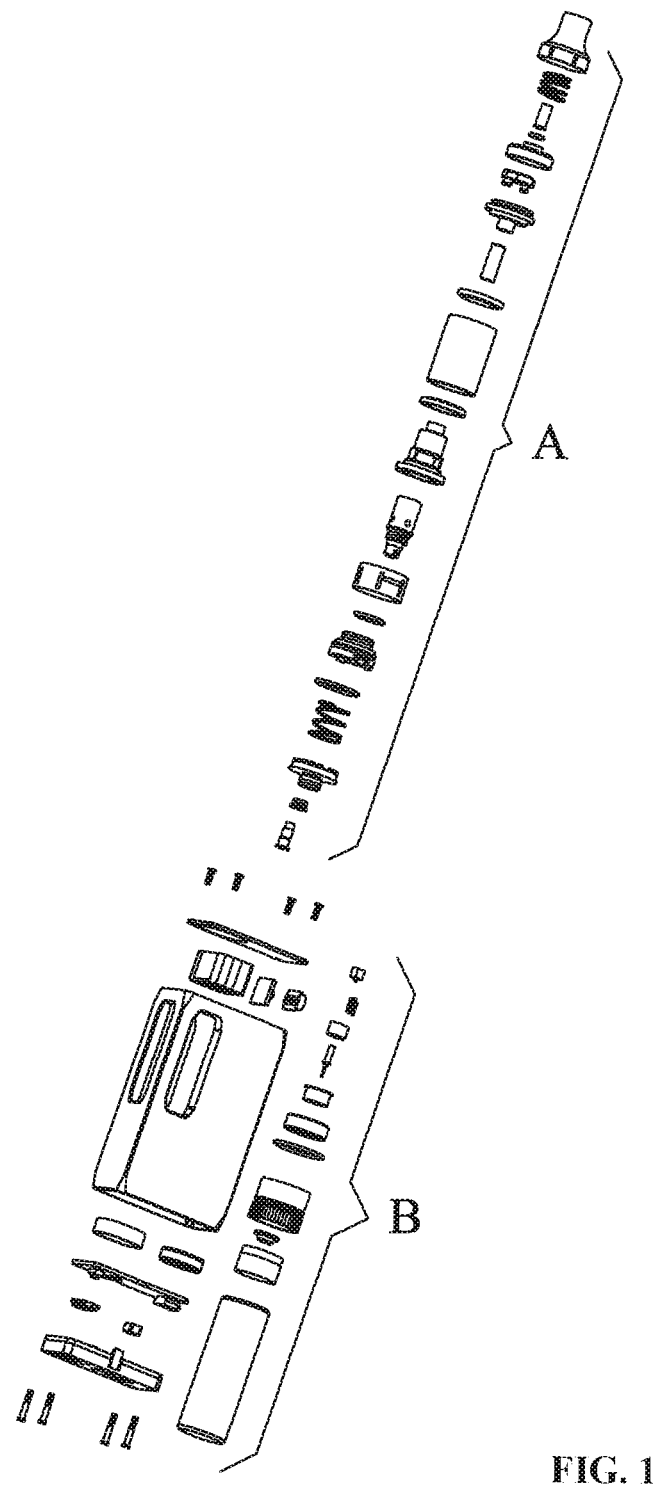
FIG. 1 is an exploded view of an electronic cigarette according to one embodiment of the disclosure.
Figure 2:
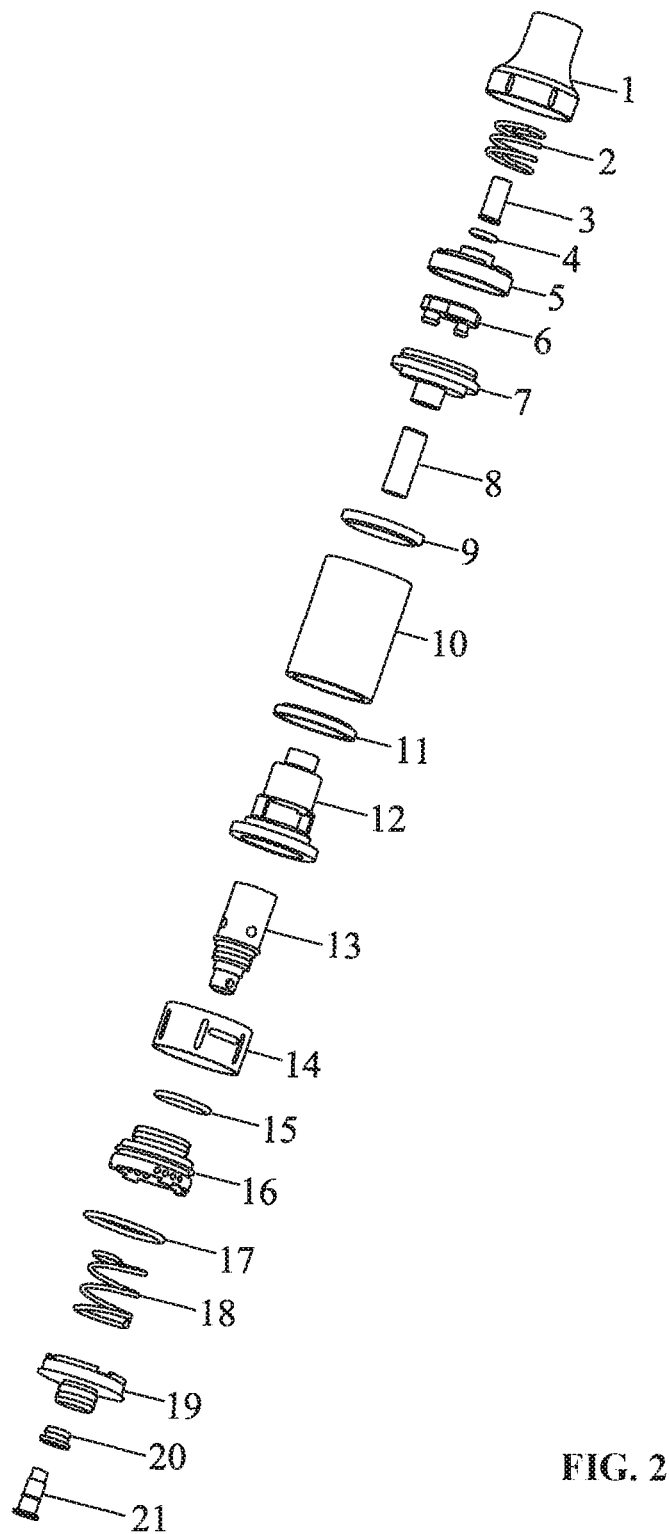
FIG. 2 is an exploded view of an atomization assembly of an electronic cigarette according to one embodiment of the disclosure.
Figure 3:
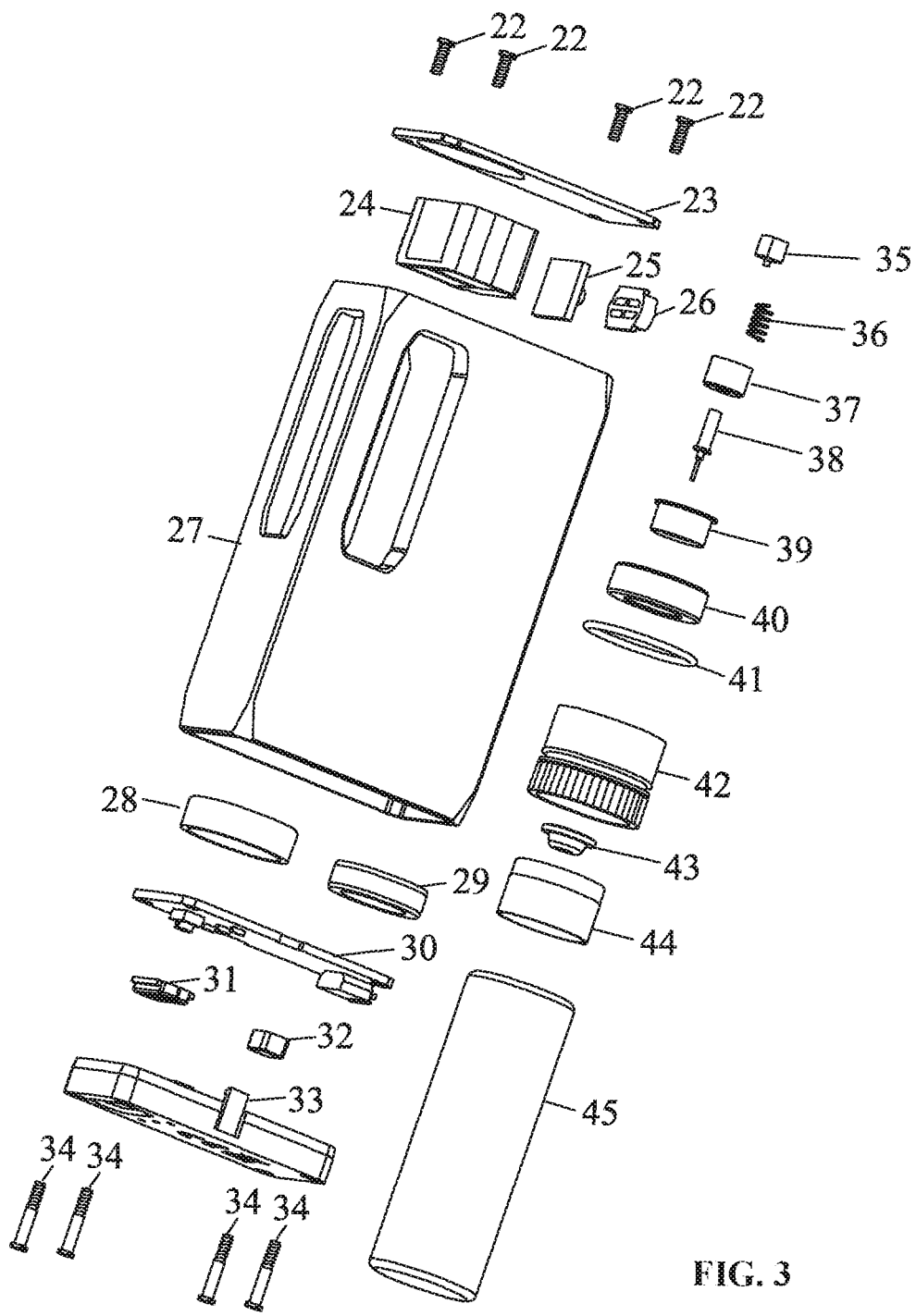
FIG. 3 is an exploded view of a battery assembly of an electronic cigarette according to one embodiment of the disclosure.
Figure 4:
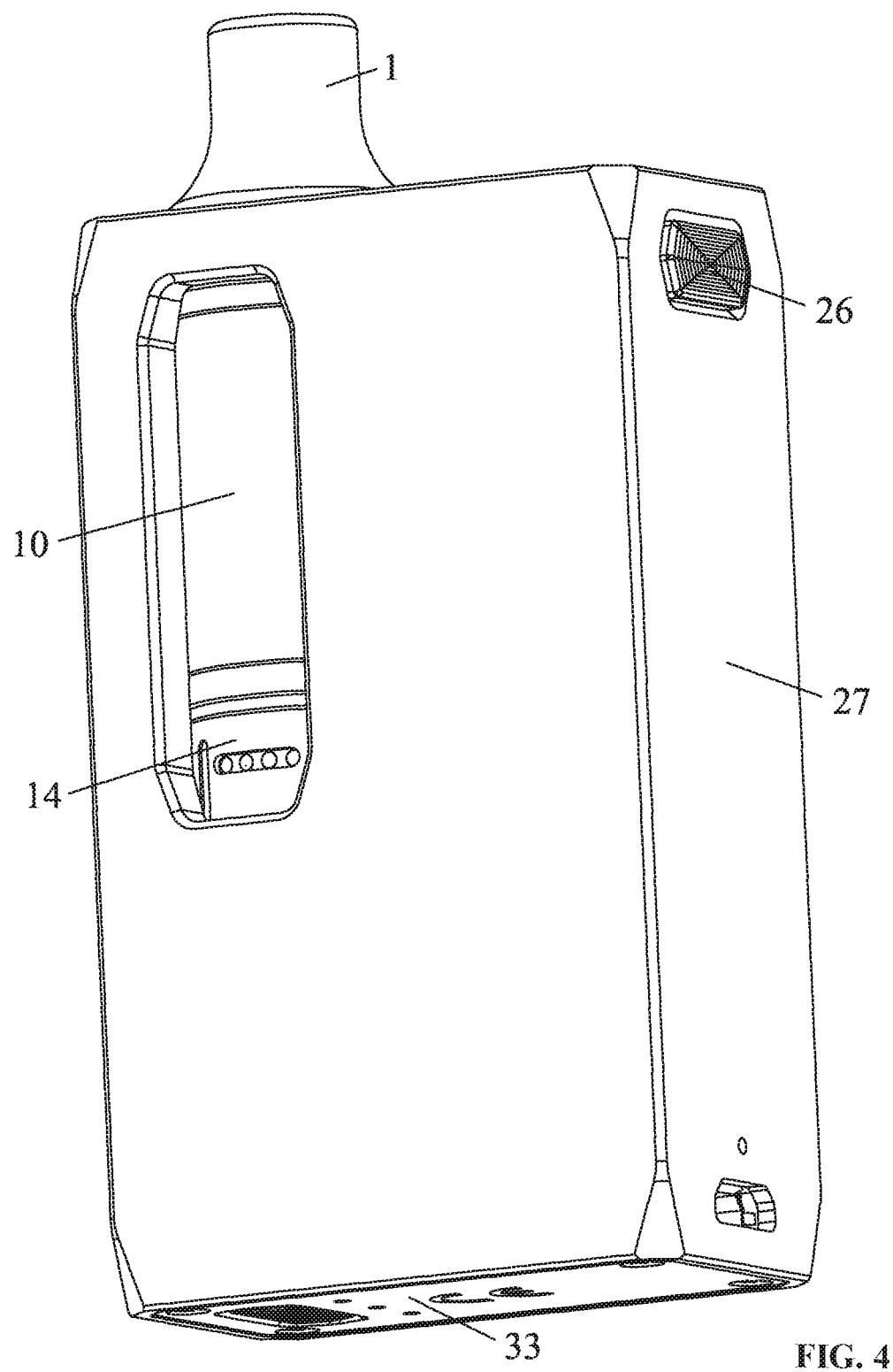
FIG. 4 is a schematic diagram of an electronic cigarette according to one embodiment of the disclosure.
Figure 5:
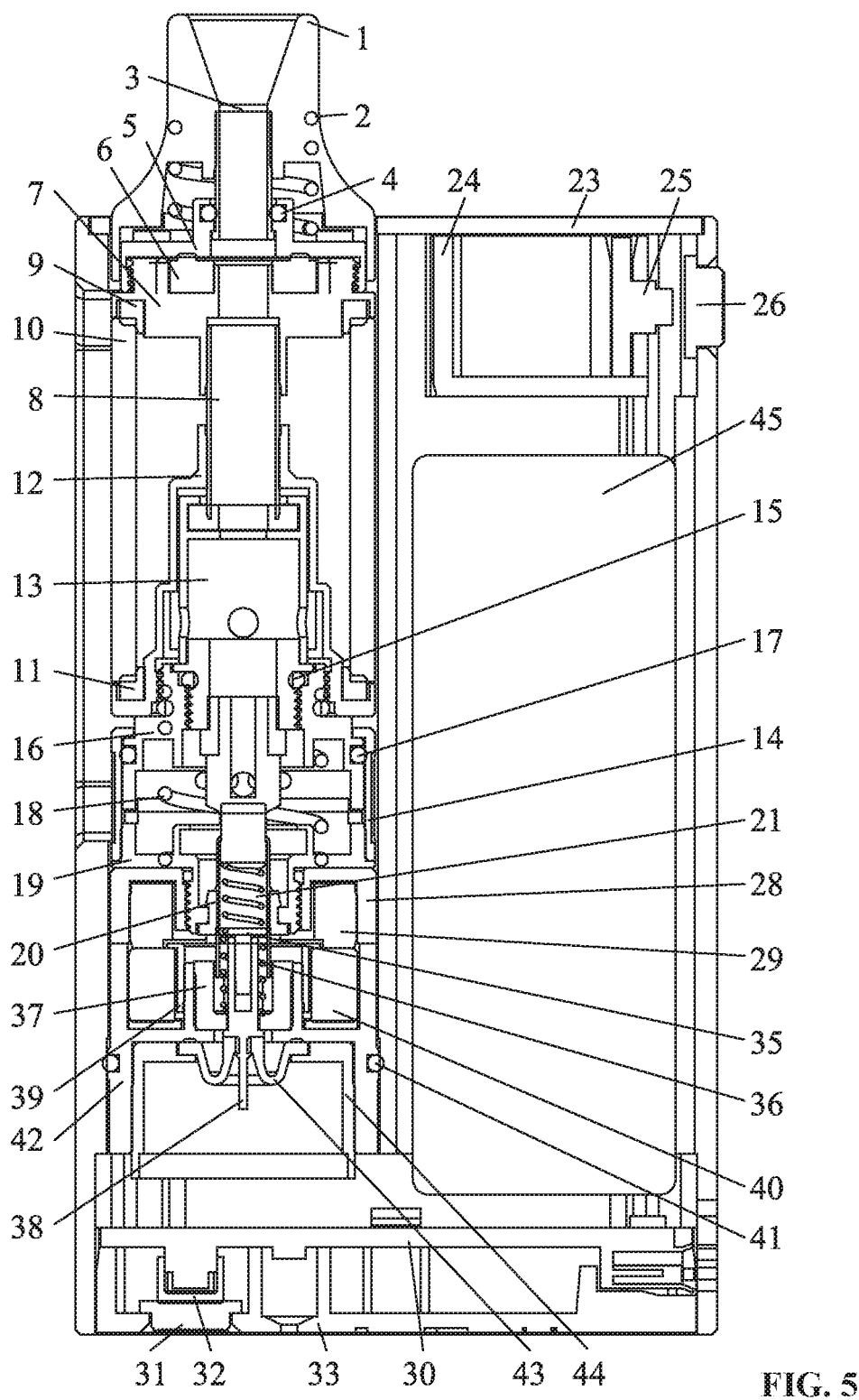
FIG. 5 is a sectional view of an electronic cigarette according to one embodiment of the disclosure.

To further illustrate, embodiments detailing an electronic cigarette are described below. It should be noted that the following embodiments are intended to describe and not to limit the disclosure.

An electronic cigarette comprises an atomization assembly A and a battery assembly B. The atomization assembly A is disposed in the battery assembly B.

The atomization assembly A comprises a mouthpiece 1; a first spring 2 disposed in a cavity of the mouthpiece 1; a first connection ring 3; a first seal ring 4 sealing the first connection ring 3; a first fixed seat 5 fixing the mouthpiece 1; a silicone gasket 6; a hollow rod 8; a first fixed ring 7 fixing the hollow rod 8; a glass tube 10; a second seal ring 9 and a third seal ring 11 sealing two ends of the glass tube 10, respectively; a second fixed ring 12 fixing the glass tube 10; an atomizer 13; a regulating ring 14; a second fixed seat 16 fixing the atomizer 13; a fourth seal ring 15 and a fifth seal ring 17 sealing two ends of the second fixed seat 16, respectively; a second spring 18; a first threaded ring 19; a first insulation ring 20 being sheathed on the atomizer 13; and a first joint 21 directly connected to the atomizer 13.

The battery assembly comprises a cover plate 23; a plurality of first screws 22 fixing the cover plate 23; a power button 26; a button board 25; a support 24; a housing 27; a second threaded ring 28; a second connection ring 29; a press plate 30; a press key 31; a silicone cap 32; a base cover 33; a plurality of second screws 34 fixing the base cover 33; a second joint 35; a second spring 36; a second insulation ring 37; a third fixed ring 38 fixing the second joint 35; a magnet 40; a fifth fixed ring 39 fixing the magnet 40; a sixth seal ring 41; an elastic fixed seat 42 fixing the second joint 35; an e-liquid blocker 43; a battery core 45; and a third connection ring 44 connected to a negative end of the battery core 45.

The first seal ring 4 is disposed on one end of the first connection ring 3; the one end of the first connection ring 3 is directly connected to the first fixed seat 5 fixing the mouthpiece 1; the first spring 2 is sheathed on the first connection ring 3; the mouthpiece 1 is fixed on the first fixed seat 5; the silicone gasket 6 and the second seal ring 9 are disposed on the first fixed ring 7; the first fixed seat 5 is in threaded connection to the first fixed ring 7; the first fixed ring 7 is in threaded connection to the glass tube 10; the hollow rod 8 is disposed on the second fixed ring 12; the third seal ring 11 is sheathed on the second fixed ring 12; the second fixed ring 12 is disposed in the glass tube 10; the first insulation ring 20 is sheathed on the first joint 21; the first joint 21 is disposed in the first threaded ring 19; the second spring 18 is disposed on the first threaded ring 19; the first threaded ring 19 is disposed in the second fixed seat 16; the fourth seal ring 15 and the fifth seal ring 17 are disposed on two ends of the second fixed seat 16, respectively; the regulating ring 14 is sheathed on the second fixed seat 16; the atomizer 13 is in threaded connection to the second fixed seat 16; and the second fixed seat 16 is in threaded connection to the second fixed ring 12.

The second spring 36 is sheathed on the third fixed ring 38; the second joint 35 is fixed on the third fixed ring 38; the second insulation ring 37 is sheathed on the second joint 35 and disposed in the fifth fixed ring 39; the fifth fixed ring 39 is disposed in the magnet 40; the magnet 40 is disposed in the elastic fixed seat 42; the e-liquid blocker 43 is disposed on one end of the third fixed ring 38; the third connection ring 44 is directly connected to the elastic fixed seat 42; the sixth seal ring 41 is disposed on the elastic fixed seat 42; the elastic fixed seat 42 is disposed in the housing 27; the battery core 45 is disposed in the housing 27; the second connection ring 29 is disposed in the second threaded ring 28 and is in magnetic connection to the magnet 40; the power button 26 is disposed on the button board 25; the button board 25 is disposed on the support 24; the support 24 is disposed in the housing 27; the cover plate 23 is fixed on the housing 27 via the plurality of first screws 22; the silicone cap 32 is disposed on the press key 31; the press key 31 is disposed on the press plate 30; the press plate 30 is disposed on the base cover 33; and the base cover 33 is fixed on the housing via the plurality of second screws 34.

In the upper part of the atomization assembly, the first fixed seat 5 is in threaded connection to the first fixed ring 7, which forms a first locking structure. In the lower part of the atomization assembly, the atomizer 13 is in threaded connection to the second fixed seat 16, and the second fixed seat 16 is in threaded connection to the second fixed ring 12, which forms a second locking structure. Thus, the atomization assembly is an integrated structure and is not easy to dismantle by children. This reduces the risk of e-liquid leakage.

The atomization assembly is disposed in the housing of the battery assembly. Specifically, the atomization assembly is in threaded connection to the second threaded ring 28, and the second threaded ring 28 is in magnetic connection to the magnet 40, so that the atomization assembly is connected to the battery assembly through magnetic attraction. This simplifies the separation of the atomization assembly from the battery assembly.

It will be obvious to those skilled in the art that changes and modifications may be made, and therefore, the aim in the appended claims is to cover all such changes and modifications.

What is claimed is:

1. A device, comprising:
   1) an atomization assembly, the atomization assembly comprising:
      a mouthpiece;
      a first spring disposed in a cavity of the mouthpiece;
      a first connection ring;
      a first seal ring sealing the first connection ring;
      a first fixed seat fixing the mouthpiece;
      a silicone gasket;
      a hollow rod;
      a first fixed ring fixing the hollow rod;
      a glass tube;
      a second seal ring and a third seal ring sealing two ends of the glass tube, respectively;
      a second fixed ring fixing the glass tube;
      an atomizer;
      a regulating ring;
      a second fixed seat fixing the atomizer;
      a fourth seal ring and a fifth seal ring sealing two ends of the second fixed seat, respectively;
      a second spring;
      a first threaded ring;
      a first insulation ring being sheathed on the atomizer; and
      a first joint directly connected to the atomizer; and
   2) a battery assembly, the battery assembly comprising:
      a cover plate;
      a plurality of first screws fixing the cover plate;
      a power button;

a button board;
a support;
a housing;
a second threaded ring;
a second connection ring;
a press plate;
a press key;
a silicone cap;
a base cover;
a plurality of second screws fixing the base cover;
a second joint;
a second spring;
a second insulation ring;
a third fixed ring fixing the second joint;
a magnet;
a fifth fixed ring fixing the magnet;
a sixth seal ring;
an elastic fixed seat fixing the second joint;
an e-liquid blocker;
a battery core; and
a third connection ring connected to a negative end of the battery core;
wherein:
  the first seal ring is disposed on one end of the first connection ring; the one end of the first connection ring is directly connected to the first fixed seat fixing the mouthpiece; the first spring is sheathed on the first connection ring; the mouthpiece is fixed on the first fixed seat;
  the silicone gasket and the second seal ring are disposed on the first fixed ring; the first fixed seat is in threaded connection to the first fixed ring; the first fixed ring is in threaded connection to the glass tube; the hollow rod is disposed on the second fixed ring; the third seal ring is sheathed on the second fixed ring; the second fixed ring is disposed in the glass tube;
  the first insulation ring is sheathed on the first joint; the first joint is disposed in the first threaded ring; the second spring is disposed on the first threaded ring; the first threaded ring is disposed in the second fixed seat; the fourth seal ring and the fifth seal ring are disposed on two ends of the second fixed seat, respectively; the regulating ring is sheathed on the second fixed seat; the atomizer is in threaded connection to the second fixed seat; and the second fixed seat is in threaded connection to the second fixed ring;
  the second spring is sheathed on the third fixed ring; the second joint is fixed on the third fixed ring; the second insulation ring is sheathed on the second joint and disposed in the fifth fixed ring; the fifth fixed ring is disposed in the magnet; the magnet is disposed in the elastic fixed seat;
  the e-liquid blocker is disposed on one end of the third fixed ring; the third connection ring is directly connected to the elastic fixed seat; the sixth seal ring is disposed on the elastic fixed seat; the elastic fixed seat is disposed in the housing; the battery core is disposed in the housing;
  the second connection ring is disposed in the second threaded ring and is in magnetic connection to the magnet;
  the power button is disposed on the button board; the button board is disposed on the support; the support is disposed in the housing;
  the cover plate is fixed on the housing via the plurality of first screws; and
  the silicone cap is disposed on the press key: the press key is disposed on the press plate; the press plate is disposed on the base cover; and the base cover is fixed on the housing via the plurality of second screws.

* * * * *